(12) United States Patent
Bennett et al.

(10) Patent No.: US 8,669,102 B2
(45) Date of Patent: Mar. 11, 2014

(54) MODULATION OF PRION EXPRESSION

(75) Inventors: C. Frank Bennett, Carlsbad, CA (US); Gene Hung, San Diego, CA (US); Susan M. Freier, San Diego, CA (US); Kenneth W. Dobie, Del Mar, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 13/059,058

(22) PCT Filed: Aug. 14, 2009

(86) PCT No.: PCT/US2009/004680
§ 371 (c)(1),
(2), (4) Date: May 3, 2011

(87) PCT Pub. No.: WO2010/019270
PCT Pub. Date: Feb. 18, 2010

(65) Prior Publication Data
US 2011/0269818 A1 Nov. 3, 2011

Related U.S. Application Data

(60) Provisional application No. 61/089,013, filed on Aug. 14, 2008.

(51) Int. Cl.
*C12N 15/85* (2006.01)
*C07H 21/04* (2006.01)
*C07H 21/02* (2006.01)

(52) U.S. Cl.
USPC ...... 435/325; 536/23.1; 536/24.3; 536/24.31; 536/24.33; 536/24.5; 514/44

(58) Field of Classification Search
None
See application file for complete search history.

(56) References Cited

U.S. PATENT DOCUMENTS

| | | | |
|---|---|---|---|
| 5,801,154 A | 9/1998 | Baracchini et al. | |
| 6,582,908 B2 | 6/2003 | Fodor et al. | |
| 7,399,845 B2* | 7/2008 | Seth et al. | 536/22.1 |
| 2001/0053519 A1 | 12/2001 | Fodor et al. | |
| 2002/0081645 A1 | 6/2002 | Collinge | |
| 2003/0228597 A1 | 12/2003 | Cowsert et al. | |
| 2005/0053583 A1 | 3/2005 | Sakaguchi et al. | |
| 2006/0280745 A1 | 12/2006 | Collinge et al. | |
| 2007/0031844 A1 | 2/2007 | Khvorova et al. | |
| 2007/0123480 A1 | 5/2007 | Juteau et al. | |
| 2008/0085269 A1 | 4/2008 | Eisenbach-Schwartz | |

OTHER PUBLICATIONS

Olie et al. (Biochemica et Biophysica Acta, 1576, 2002, 101-109).*
Branch et al., "A good antisense molecule is hard to find," TIBS (1998) 23:45-50.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles'of Antisense Therapeutics" Antisense Research and Application (1998) Chapter 1:1-50.
Daude et al., "Specific inhibition of pathological prion protein accumulation by small interfering RNAs" Journal of Cell Science (2003) 116(13):2775-2779.
Golding et al., "Suppression of prion protein in livestock by RNA interference" PNAS (2006) 103(14):5285-5290.
Kapui et al., "Phosphorothioate Oligonucleotides Reduce PrPsc Levels and Prion Infectivity in Cultured Cells" Mol Med (2007) 13(3-4):190-198.
Ohnishi et al., "Enhancement of Allele Discrimination by Introduction of Nucleotide Mismatches into siRNA in Allele-Specific Gene Silencing by RNAi" PLoS One (2008) 3(5):e2248.
Pfeifer et al., "Lentivector-mediated RNAi efficiently suppresses prion protein and prolongs survival of scrapie-infected mice" J. Clin. Invest. (2006) 116(12):3204-3210.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sutou et al., "Knockdown of the bovine prion gene PRNP by RNA interference (RNAi) technology" BMC Biotechnology (2007) 7:44.
Tilly et al., "Efficient and specific down-regulation of prion protein expression by RNAi" Biochemical and Biophysical Research Communications (2003) 305:548-551.
Weiss et al., "RNA Aptamers Specifically Interact with the Prion Protein PrP" Journal of Virology (1997) 71(11):8790-8797.
White et al., "Single treatment with RNAi against prion protein rescues early neuronal dysfunction and prolongs survival in mice with prion diseases" PNAS (2008) 105(29):10238-10243.
International Search Report for application PCT/US2009/004680 dated Oct. 13, 2009.

* cited by examiner

*Primary Examiner* — Amy Bowman
(74) *Attorney, Agent, or Firm* — Jones Day

(57) ABSTRACT

Disclosed herein are compounds and methods for decreasing PrP and preventing, ameliorating, or treating a prion disease or conformational neurodegenerative disorder, in an individual in need thereof. Examples of disease conditions that can be ameliorated with the administration of antisense compounds targeted to PrP include Creutzfeldt-Jakob disease (CJD); variant Creutzfeldt-Jakob Disease (vCJD); Gerstmann-Straussler-Scheinker syndrome; fatal familial insomnia; kuru; Bovine Spongiform Encephalopathy (BSE), e.g. "mad cow disease"; Chronic Wasting Disease (CWD); scrapie; transmissible mink encephalopathy; feline spongiform encephalopathy; ungulate spongiform encephalopathy; Alzheimer's disease; Parkinson's disease; Huntington's disease; and Amyotrophic Lateral Sclerosis (ALS).

30 Claims, No Drawings

MODULATION OF PRION EXPRESSION

REFERENCE TO RELATED APPLICATION

This application is a national stage application filed under 35 U.S.C §371(f) of International Application No. PCT/US2009/004680, filed Aug. 14, 2009, which claims benefit under 35 U.S.C. §119(e) of U.S. Provisional Application No. 61/089,013, filed Aug. 14, 2008.

SEQUENCE LISTING

The present application is being filed along with a Sequence Listing in electronic format. The Sequence Listing is provided as a file entitled 12207089999_SeqList.txt, created Feb. 14, 2011, which is 14 Kb in size. The information in the electronic format of the sequence listing is incorporated herein by reference in its entirety.

FIELD OF THE INVENTION

The present invention provides compounds and methods for decreasing prion protein (PrP) expression and for the treatment of prion diseases and other conformational neurodegenerative disorders.

BACKGROUND OF THE INVENTION

Prion diseases are a family of rare progressive neurodegenerative disorders that affect both humans and animals. Such diseases are caused by prions and are distinguished by long incubation periods, characteristic spongiform changes associated with neuronal loss, and a failure to induce inflammatory response.

Prions are the causative agents of transmissible spongiform encephalopathies. A prion is an infectious, abnormal, proteinaceous, transmissible agent that is able to induce abnormal folding of normal cellular prion proteins in the brain, leading to brain damage and the characteristics signs and symptoms of prion disease. Prion diseases are usually rapidly progressive and always fatal.

The prion proteins can occur in both a normal cellular form, which is a harmless protein found in the body's cells, and in an infectious form, which causes disease. The harmless and infectious forms of the prion protein have the same amino acid sequence. However, the infectious form of the protein takes a different conformational form than the normal protein. Sporadic prion diseases may develop when an individual's normal prion proteins spontaneously change into the infectious form of the protein and subsequently alter prion proteins in other cells in a chain reaction. Once they appear, abnormal prion proteins aggregate, or clump together.

About 5 to 10 percent of all Creutzfeldt-Jakob Disease (CJD) cases are inherited. These cases arise from a mutation in the gene that controls formation of the normal prion protein. While prions themselves do not contain genetic information and do not require genes to reproduce themselves, infectious prions can arise if a mutation occurs in the gene for the individual's normal prion protein. Several different mutations in the prion gene have been identified. The particular mutation found in each family affects how frequently the disease appears and what symptoms are most noticeable.

Other risk factors and causes of prion diseases include, but are not limited to, age; exposure to contaminated meat, such as beef; and exposure to contaminated body tissues, such as, human growth hormone, dura mater, corneas, spinal cord, brain tissue, and central nervous system (CNS) fluid.

SUMMARY OF THE INVENTION

Provided herein are methods, agents, and compositions for modulating prion protein (PrP). The agents and compositions include PrP-specific inhibitors. In certain embodiments, PrP-specific inhibitors are nucleic acids.

Also provided are methods of preventing, treating, and ameliorating diseases and disorders. Included are methods of treating prion diseases. The diseases and disorders include, but are not limited to, those associated with spongiform changes, development of abnormal protein aggregates, neuronal loss, and failure to induce inflammatory response.

Also provided are methods of treating multiple diseases or disorders. The multiple diseases or disorders can include any of the diseases and disorders provided herein. The multiple diseases and disorders can have one or more risk factors, causes, or outcomes in common. Such diseases include prion diseases, such as, but not limited to, Creutzfeldt-Jakob disease (CJD); variant Creutzfeldt-Jakob Disease (vCJD); Gerstmann-Straussler-Scheinker syndrome; fatal familial insomnia; kuru; Bovine Spongiform Encephalopathy (BSE), e.g. "mad cow disease"; Chronic Wasting Disease (CWD); scrapie; transmissible mink encephalopathy; feline spongiform encephalopathy; and ungulate spongiform encephalopathy. Certain risk factors and causes of prion diseases include, but are not limited to, age; exposure to contaminated meat, such as beef; and exposure to contaminated body tissues, such as, human growth hormone, dura mater, corneas, spinal cord, brain tissue, and central nervous system (CNS) fluid. Certain outcomes include, but are not limited to, dementia; lack of muscle coordination; personality changes, including, impaired memory, judgment, and thinking; impaired vision; insomnia; depression; unusual sensations; myoclonus; blindness; loss of speech; or coma.

Also provided are methods of treating conformational neurodegenerative disorders, such as, but not limited to, Alzheimer's disease, Parkinson's disease, Huntington's disease, and Amyotrophic Lateral Sclerosis (ALS).

In certain embodiments, methods of treatment include administering to a subject a PrP-specific inhibitor.

Methods of modulating PrP include methods of modulating levels of PrP mRNA and levels of PrP protein. Modulation can occur in a cell or tissue. In certain embodiments, the cell or tissue is in an animal. In certain embodiments, the animal is a human. In certain embodiments, PrP levels are reduced. Such reduction can occur in a time-dependent manner or in a dose-dependent manner or both.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical ingredient" means the substance or substances in a pharmaceutical composition that provides a desired effect.

"Administered concomitantly" refers to the co-administration of at least two agents or therapies in any manner in which the pharmacological effects of both are manifest in the patient at the same time or over the same time period. Concomitant administration does not require that both agents be administered in a single pharmaceutical composition, in the same dosage form, or by the same route of administration.

"Administering" means providing a pharmaceutical agent to an individual, and includes, but is not limited to administering by a medical professional and self-administering.

"Amelioration" refers to a lessening of at least one indicator, sign, or symptom of an associated condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense compound" means an oligomeric compound that is capable of undergoing hybridization to a target nucleic acid through hydrogen bonding.

"Antisense inhibition" means reduction of target nucleic acid levels in the presence of an antisense compound complementary to the target nucleic acid compared to target nucleic acid levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chimeric antisense compound" means an antisense compound that has at least 2 chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Conformational neurodegenerative disorders" refers to disorders and diseases characterized by misfolded proteins. In certain embodiments, conformational neurodegenerative disorders include, prion diseases, as well as Alzheimer's disease, Parkinson's disease, Huntington's disease, and Amyotrophic Lateral Sclerosis (ALS).

"Contiguous nucleobases" means nucleobases immediately adjacent to each other.

"Diluent" means an ingredient in a composition that lacks pharmacological activity, but is pharmaceutically necessary or desirable. For example, in agents that are injected the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments, where subcutaneous administration is desired, the desired dose requires a volume not easily accommodated by a single injection. In certain embodiments, two or more injections may be used to achieve the desired dose. In certain embodiments, a dose may be administered in one, two, or more injections to minimize injection site reaction in an individual. In certain embodiments, the pharmaceutical agent is administered by infusion over an extended period of time or continuously. Doses may be stated as the amount of pharmaceutical agent per hour, day, week or month.

"Effective amount" in the context of modulating an activity or of treating or preventing a condition means the administration of that amount of active ingredient to a subject in need of such modulation, treatment or prophylaxis, either in a single dose or as part of a series, that is effective for modulation of that effect, or for treatment or prophylaxis or improvement of that condition. The effective amount will vary depending upon the health and physical condition of the subject to be treated, the taxonomic group of subjects to be treated, the formulation of the composition, the assessment of the medical situation, and other relevant factors.

"Fully complementary" means each nucleobase of a first nucleic acid has a complementary nucleobase in a second nucleic acid. In certain embodiments, a first nucleic acid is an antisense compound and a target nucleic acid is a second nucleic acid. In certain embodiments, an antisense oligonucleotide is a first nucleic acid and a target nucleic acid is a second nucleic acid.

"Gapmer" means an antisense compound in which an internal position having a plurality of nucleotides that supports RNaseH cleavage is positioned between external regions having one or more nucleotides that are chemically distinct from the nucleosides of the internal region. A "gap segment" means the plurality of nucleotides that make up the internal region of a gapmer. A "wing segment" means the external region of a gapmer.

"Gap-widened" means an antisense compound has a gap segment of 12 or more contiguous 2'-deoxyribonucleotides positioned between and immediately adjacent to 5' and 3' wing segments having from one to six nucleotides having modified sugar moieties.

"Hybridization" means the annealing of complementary nucleic acid molecules. In certain embodiments, complementary nucleic acid molecules include, but are not limited to, an antisense compound and a nucleic acid target. In certain embodiments, complementary nucleic acid molecules include, but are not limited to, an antisense oligonucleotide and a nucleic acid target.

"Immediately adjacent" means there are no intervening nucleotides between the immediately adjacent elements.

"Intracerebroventricular administration" means administration through injection or infusion into the ventricular system of the brain.

"Intraperitoneal administration" means administration to the peritoneal cavity.

"Intrathecal administration" means administration through injection or infusion into the cerebrospinal fluid bathing the spinal cord and brain.

"Identifying an animal having a conformational neurodegenerative disorder" means identifying an animal having been diagnosed with a conformational neurodegenerative disorder; or, identifying an animal having any symptom of a conformational neurodegenerative disorder including, but not limited to, dementia; lack of muscle coordination; personality changes, including, impaired memory, judgment, and thinking; impaired vision; insomnia; depression; unusual sensations; myoclonus; blindness; loss of speech; or coma. Such identification may be accomplished by any method, including but not limited to, standard clinical tests or assessments, such as psychiatric evaluation, neurological evaluation, electroencephalogram, spinal tap, computerized tomography, magnetic resonance imaging (MRI) brain scans, brain biopsy, and the like. In some cases the clinical tests and assessments are not used to affirmatively diagnose conformational neurodegenerative disorders, but rather are used to rule out other neurological diseases.

"Identifying an animal having a prion disease" means identifying an animal having been diagnosed with a prion disease; or, identifying an animal having any symptom of a prion disease including, but not limited to, dementia; lack of muscle coordination; personality changes, including, impaired memory, judgment, and thinking; impaired vision; insomnia; depression; unusual sensations; myoclonus; blindness; loss of speech; or coma. Such identification may be accomplished by any method, including but not limited to, standard clinical tests or assessments, such as psychiatric evaluation, neurological evaluation, electroencephalogram, spinal tap, computerized tomography, magnetic resonance imaging (MRI) brain scans, brain biopsy, and the like. In some cases the clinical tests and assessments are not used to affirmatively diagnose prion disease, but rather are used to rule out other neurological diseases.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" means a nucleobase of first nucleic acid that is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or any change from a natural sugar.

"Motif" means the pattern of unmodified and modified nucleosides in an antisense compound.

"Naturally occurring internucleoside linkage" means a 3' to 5' phosphodiester linkage.

"Natural sugar" means a sugar found in DNA (2'-H) or RNA (2'-OH).

"Neurodegenerative diseases" refer to a varied assortment of central nervous system disorders characterized by gradual and progressive loss of neural tissue.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" means a polymer of linked monomeric subunits which is capable of hybridizing to at least a region of a nucleic acid molecule.

"Oligonucleoside" means an oligonucleotide in which the internucleoside linkages do not contain a phosphorus atom.

"Oligonucleotide" means a polymer of linked nucleosides each of which can be modified or unmodified, independent one from another.

"Parenteral administration," means administration through injection or infusion. Parenteral administration includes, but is not limited to, subcutaneous administration; intravenous administration; intraarterial administration; intraperitoneal administration; intramuscular administration; or intracranial administration, e.g., intrathecal or intracerebroventricular administration.

"Peptide" means a molecule formed by linking at least two amino acids by amide bonds. Without limitation, as used herein, "peptide" refers to polypeptides and proteins.

"Pharmaceutical agent" means a substance that provides a therapeutic benefit when administered to an individual. For example, in certain embodiments, an antisense oligonucleotide targeted to PrP is pharmaceutical agent.

"Pharmaceutical composition" means a mixture of substances suitable for administering to an individual. For example, a pharmaceutical composition may comprise one or more antisense oligonucleotides and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate internucleoside linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a condition or disease for a period of time from hours to years.

"Prion" means an abnormal, transmissible agent that is able to induce abnormal folding of normal cellular prion proteins in the brain, leading to brain damage and the characteristics signs and symptoms of prion disease.

"Prion disease" refers to a family of rare progressive neurodegenerative disorders that affect both humans and animals caused by prions. Prion disease are distinguished by long incubation periods, characteristic spongiform changes associated with neuronal loss, and a failure to induce inflammatory response. In certain embodiments, prion diseases include Alzheimer's disease, Creutzfeldt-Jakob disease (CJD); variant Creutzfeldt-Jakob Disease (vCJD); Gerstmann-Straussler-Scheinker syndrome; fatal familial insomnia; kuru; Bovine Spongiform Encephalopathy (BSE), e.g. "mad cow disease"; Chronic Wasting Disease (CWD); scrapie; transmissible mink encephalopathy; feline spongiform encephalopathy; and ungulate spongiform encephalopathy.

"Prodrug" means a therapeutic agent that is prepared in an inactive form that is converted to an active form (i.e., drug) within the body or cells thereof by the action of endogenous enzymes or other chemicals or conditions.

"PrP-specific inhibitor" or "PrP inhibitor" means any compound capable of decreasing PrP mRNA or protein expression. Examples of such compounds include a nucleic acid, a peptide, and an antibody.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" means when there is a sufficient degree of complementarity between an antisense compound and a target sequence to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

"Subcutaneous administration" means administration just below the skin. "Intravenous administration" means administration into a vein.

"Targeted" or "targeted to" means having a nucleobase sequence that will allow hybridization of an antisense compound to a target molecule to induce a desired effect. In certain embodiments, a desired effect is reduction of a target nucleic acid. In certain embodiments, a desired effect is reduction of PrP mRNA or protein expression.

"Targeting" means the process of design and selection of an antisense compound that will specifically hybridize to a target nucleic acid and induce a desired effect.

"Target nucleic acid," "target RNA," "target RNA transcript" and "nucleic acid target" all mean a nucleic acid capable of being targeted by antisense compounds.

"Target region" means a portion of a target nucleic acid to which one or more antisense compounds is targeted.

"Target segment" refers to a smaller portion or sub-portion of a region within a target nucleic acid. A target segment can be the sequence of nucleotides of a target nucleic acid to which an antisense compound is targeted.

"Therapeutically effective amount" means an amount of a pharmaceutical agent that provides a therapeutic benefit to an individual.

"Treat" refers to administering a composition of the invention to effect an alteration or improvement of the disease or condition. Prevention, amelioration, or treatment may require administration of multiple doses at regular intervals, or prior to onset of the disease or condition to alter the course of the disease or condition. Moreover, a single agent may be used in a single individual for each prevention, amelioration, and treatment of a condition or disease sequentially, or concurrently.

"Unmodified nucleotide" means a nucleotide composed of naturally occurring nucleobases, sugar moieties and internucleoside linkages. In certain embodiments, an unmodified nucleotide is an RNA nucleotide (i.e., β-D-ribonucleosides) or a DNA nucleotide (i.e., β-D-deoxyribonucleoside).

Certain Embodiments

The present invention provides compounds and methods for decreasing prion protein (PrP) expression and for the treatment of prion diseases and other conformational neurodegenerative disorders. Also contemplated are compounds and methods for the prevention or slowing of prion replication in an individual in need thereof. Also contemplated are compounds and methods for the treatment, amelioration, or prevention of prion infection in an individual in need thereof. Also contemplated are compounds and methods for the treatment, amelioration, or prevention of neurological degeneration associated with prion infection in an individual in need thereof. Also contemplated are compounds and methods for the preparation of a medicament for the treatment, amelioration, or prevention of prion disease. Such compositions and methods are useful for treating, ameliorating, or preventing prion diseases, such as, but not limited to, Creutzfeldt-Jakob disease (CJD); variant Creutzfeldt-Jakob Disease (vCJD); Gerstmann-Straussler-Scheinker syndrome; fatal familial insomnia; kuru; Bovine Spongiform Encephalopathy (BSE), e.g. "mad cow disease"; Chronic Wasting Disease (CWD); scrapie; transmissible mink encephalopathy; feline spongiform encephalopathy; and ungulate spongiform encephalopathy. Such compositions and methods are also useful for treating, ameliorating, or preventing other conformational neurodegenerative disorders, such as, but not limited to, Alzheimer's disease, Parkinson's disease, Huntington's disease, and Amyotrophic Lateral Sclerosis (ALS).

The present invention provides a PrP-specific inhibitor as described herein for use in treating, ameliorating, or preventing a prion disease, as described herein. For example, the invention provides a PrP-specific inhibitor as described herein for use in treating, ameliorating, or preventing Creutzfeldt-Jakob disease (CJD); variant Creutzfeldt-Jakob Disease (vCJD); Gerstmann-Straussler-Scheinker syndrome; fatal familial insomnia; kuru; Bovine Spongiform Encephalopathy (BSE), e.g. "mad cow disease"; Chronic Wasting Disease (CWD); scrapie; transmissible mink encephalopathy; feline spongiform encephalopathy; and ungulate spongiform encephalopathy.

The present invention also provides a PrP-specific inhibitor as described herein for use in treating, ameliorating, or preventing conformational neurodegenerative disorders, such as, but not limited to, Alzheimer's disease, Parkinson's disease, Huntington's disease, and Amyotrophic Lateral Sclerosis (ALS).

The present invention also provides the use of a PrP-specific inhibitor as described herein in the manufacture of a medicament for treating, ameliorating, or preventing a prion disease as described herein. For example, the invention provides the use of a PrP-specific inhibitor as described herein in the manufacture of a medicament for treating, ameliorating, or preventing CJD, vCJD, Gerstmann-Straussler-Scheinker syndrome, fatal familial insomnia, kuru, BSE, CWD, scrapie, transmissible mink encephalopathy, feline spongiform encephalopathy, and ungulate spongiform encephalopathy.

The present invention also provides the use of a PrP-specific inhibitor as described herein in the manufacture of a medicament for treating, ameliorating, or preventing conformational neurodegenerative disorders, such as, but not limited to, Alzheimer's disease, Parkinson's disease, Huntington's disease, and ALS.

The invention also provides a PrP-specific inhibitor as described herein for treating, ameliorating, or preventing aggregate formation. The present invention also provides the use of a PrP-specific inhibitor as described herein in the manufacture of a medicament for treating, ameliorating, or preventing aggregate formation.

The invention also provides a PrP-specific inhibitor as described herein for preventing, ameliorating, or treating encephalopathy. The present invention also provides the use of a PrP-specific inhibitor as described herein in the manufacture of a medicament treating, ameliorating, or preventing encephalopathy.

The invention also provides a PrP-specific inhibitor as described herein for use in treating, ameliorating, or preventing a prion disease, as described herein by combination therapy with an additional agent or therapy as described herein. Agents or therapies can be co-administered or administered concomitantly.

The invention also provides a pharmaceutical composition comprising a PrP-specific inhibitor as described herein in combination with an additional agent or therapy as described herein. Agents or therapies can be co-administered or administered concomitantly.

The invention also provides the use of a PrP-specific inhibitor as described herein in the manufacture of a medicament treating, ameliorating, or preventing a prion disease or a conformational neurodegenerative disorder as described herein by combination therapy with an additional agent or therapy as described herein. Agents or therapies can be co-administered or administered concomitantly.

The invention also provides the use of a PrP-specific inhibitor as described herein in the manufacture of a medicament for treating, ameliorating, or preventing a prion disease or a conformational neurodegenerative disorder, as described herein in a patient who has previously been administered an additional agent or therapy as described herein. Agents or therapies can be co-administered or administered concomitantly.

The invention also provides the use of a PrP-specific inhibitor as described herein in the manufacture of a medicament treating, ameliorating, or preventing a prion disease or a conformational neurodegenerative disorder, as described herein in a patient who is subsequently to be administered an additional therapy as described herein.

The invention also provides a kit for treating, ameliorating, or preventing a prion disease or a conformational neurodegenerative disorder, as described herein, wherein said kit comprises:

(i) a PrP-specific inhibitor as described herein; and alternatively
(ii) an additional therapy as described herein.

A kit of the invention may further include instructions for using the kit to treat, ameliorate, or prevent a prion disease or a conformational neurodegenerative disorder, as described herein by combination therapy as described herein.

Antisense compounds described herein may comprise an oligonucleotide consisting of 12 to 30 linked nucleosides targeted to a PrP nucleic acid. In certain embodiments, the PrP nucleic acid may be any of the sequences set forth in GENBANK Accession No. NM_000311.3 and GENBANK accession number NM_011170.1.

Also described herein are methods for treating, ameliorating, or preventing an animal having a prion disease or a conformational neurodegenerative disorder.

In certain embodiments, the method comprises identifying an animal having a prion disease and administering to the animal having prion disease a therapeutically effective amount of a PrP inhibitor.

In certain embodiments, the method comprises identifying an animal having a conformational neurodegenerative disorder and administering to the animal having a conformational neurodegenerative disorder a therapeutically effective amount of a PrP inhibitor.

In certain embodiments, the PrP inhibitor is an antisense compound.

In certain embodiments, the antisense compound is a nucleic acid.

In certain embodiments, the nucleic acid is a modified oligonucleotide.

In certain embodiments, the modified oligonucleotide may be a single-stranded or double-stranded oligonucleotide. The modified oligonucleotide may be 70, 75, 80, 85, 90, 95, or 100% complementary to a human PrP nucleic acid.

The modified oligonucleotide may have at least one modified internucleoside linkage. The internucleoside linkage may be a phosphorothioate internucleoside linkage.

The modified oligonucleotide may have at least one modified sugar. The modified sugar may be a bicyclic sugar. The modified sugar may comprise a 2'-O-methoxyethyl.

The modified oligonucleotide may comprise at least one nucleoside having a modified nucleobase.

The modified oligonucleotide may have the nucleobase sequence of any of SEQ ID NO: 3 to 39.

In certain embodiments, the method comprises identifying an animal having a prion disease and administering to the animal having prion disease a therapeutically effective amount of a compound comprising a modified oligonucleotide consisting of 12 to 30 linked nucleosides, wherein the modified oligonucleotide is complementary to human PrP.

In certain embodiments, the prion disease is CJD, vCJD, Gerstmann-Straussler-Scheinker syndrome, fatal familial insomnia, kuru, BSE, CWD, scrapie, transmissible mink encephalopathy, feline spongiform encephalopathy, or ungulate spongiform encephalopathy.

In certain embodiments, the method comprises identifying an animal having a conformational neurodegenerative disease and administering to the animal having a conformational neurodegenerative disease a therapeutically effective amount of a compound comprising a modified oligonucleotide consisting of 12 to 30 linked nucleosides, wherein the modified oligonucleotide is complementary to human PrP.

In certain embodiments, the conformational neurodegenerative disorder is Alzheimer's disease, Parkinson's disease, Huntington's disease, or ALS.

In certain embodiments the method results in a reduction of aggregates.

In certain embodiments, the method results in a reduction of aggregates by at least 20, 30, 40, 50, 60, 70, 80, 90, or 100%.

In certain embodiments the method results in increased lifespan.

In certain embodiments, the method results in an increased lifespan of days. In certain embodiments, the method results in an increased lifespan of weeks. In certain embodiments, the method results in an increased lifespan of years. In certain embodiments, the method results in an increased lifespan of decades.

In certain embodiments the method results in improved cognitive ability.

In certain embodiments the method results in improved motor function.

Antisense Compounds

Antisense compounds include, but are not limited to, oligomeric compounds, oligonucleotides, oligonucleosides, oligonucleotide analogs, oligonucleotide mimetics, antisense oligonucleotides, and siRNAs. Antisense compounds may target a nucleic acid, meaning that the antisense compound is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain embodiments an antisense oligonucleotide has a nucleobase sequence that, when written in the 5' to 3' direction, comprises the reverse complement of the target segment of a target nucleic acid to which it is targeted.

In certain embodiments an antisense compound targeted to a PrP nucleic acid is 12 to 30 subunits in length. In other words, antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments, the linked subunits are linked nucleobases, nucleosides, or nucleotides. In certain embodiments, the antisense compound is an antisense oligonucleotide, and the linked subunits are nucleotides.

In certain embodiments, a shortened or truncated antisense compound targeted to a PrP nucleic acid has a single subunit deleted from the 5' end (5' truncation), or alternatively from the 3' end (3' truncation). A shortened or truncated antisense compound targeted to a PrP nucleic acid may have two subunits deleted from the 5' end, or alternatively may have two subunits deleted from the 3' end, of the antisense compound. Alternatively, the deleted subunits may be dispersed throughout the antisense compound, for example, in an antisense compound having one subunit deleted from the 5' end and one subunit deleted from the 3' end. In certain embodiments, the subunits are nucleobases, nucleosides, or nucleotides.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end. In certain embodiments, the subunits are nucleobases, nucleosides, or nucleotides.

It is possible to increase or decrease the length of an antisense compound, such as an antisense oligonucleotide, or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a PrP nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleosides that supports RNaseH cleavage is positioned between external regions having a plurality of nucleosides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may, in certain embodiments, include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)_n$—O-2' bridge, where n=1 or n=2). In certain embodiments, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. Any of the antisense compounds described herein can have a gapmer motif. In certain embodiments, X and Z are the same, in certain other embodiments, they are different. In certain embodiments, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers of the present invention include, but are not limited to, for example 5-10-5, 4-8-4, 4-12-3, 4-12-4, 3-14-3, 2-16-2, 1-18-1, 3-10-3, 2-10-2, 1-10-1 or 2-8-2.

In certain embodiments, the antisense compound as a "wingmer" motif, having a wing-gap or gap-wing configuration, i.e. an X-Y or Y-Z configuration as described above for the gapmer configuration. Thus, wingmer configurations of the present invention include, but are not limited to, for example 5-10, 8-4,4-12, 12-4,3-14, 16-2, 18-1, 10-3,2-10, 1-10 or 8-2.

In certain embodiments, antisense compounds targeted to a PrP nucleic acid possess a 5-10-5 gapmer motif.

In certain embodiments, an antisense compound targeted to a PrP nucleic acid has a gap-widened motif. In other embodiments, an antisense oligonucleotide targeted to a PrP nucleic acid has a gap-widened motif.

In certain embodiments, a gap-widened antisense oligonucleotide targeted to a PrP nucleic acid has a gap segment of fourteen 2'-deoxyribonucleotides positioned between wing segments of three chemically modified nucleosides. In certain embodiments, the chemical modification comprises a 2'-sugar modification. In certain embodiments, the chemical modification comprises a 2'-MOE sugar modification.

Target Nucleic Acids, Target Regions and Nucleotide Sequences

Nucleotide sequences that encode PrP include, without limitation, the following: GENBANK Accession No. NM_000311.3, first deposited with GENBANK on Mar. 24, 1999, and incorporated herein as SEQ ID NO: 1 and GENBANK accession number NM_011170.1, first deposited with GENBANK on Mar. 1, 2001, and incorporated herein as SEQ ID NO: 2.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the nucleic acid. For example, a target region may encompass a 3' UTR, a 5' UTR, an exon, an intron, a coding region, a translation initiation region, translation termination region, or other defined nucleic acid region. The structurally defined regions for PrP can be obtained by accession number from sequence databases such as NCBI and such information is incorporated herein by reference. In certain other embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain other embodiments, the desired effect is reduction of levels of protein encoded by the target nucleic acid or a phenotypic change associated with the target nucleic acid. In certain embodiments, the reduction is 70% or greater, 75% or greater, 80% or greater, 85% or greater, 90% or greater, 95% or greater, or 100% at a concentration of 100 nM in T-24 cells.

A target region may contain one or more target segments. Multiple target segments within a target region may be overlapping. Alternatively, they may be non-overlapping. In certain embodiments, target segments within a target region are separated by no more than about 300 nucleotides. In other embodiments, target segments within a target region are separated by no more than about, 250, 200, 150, 100, 90, 80, 70, 60, 50, 40, 30, 20, or 10 nucleotides on the target nucleic acid. In certain embodiments, target segments within a target region are separated by no more than about 5 nucleotides on the target nucleic acid. In certain embodiments, target segments are contiguous.

Suitable target segments may be found within a 5' UTR, a coding region, a 3' UTR, an intron, or an exon. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in PrP mRNA levels are indicative of inhibition of PrP expression. Reductions in levels of a PrP protein are also indicative of inhibition of target mRNA expression. Further, phenotypic changes are indicative of inhibition of PrP expression. For example, phenotypic changes may include reduction in aggregates, increase in lifespan, improved cognitive ability, and improved motor function.

Hybridization

In certain embodiments, hybridization occurs between an antisense compound disclosed herein and a PrP nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a PrP nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a PrP nucleic acid).

Non-complementary nucleobases between an antisense compound and a PrP nucleic acid may be tolerated provided that the antisense compound remains able to specifically hybridize to a target nucleic acid. Moreover, an antisense compound may hybridize over one or more segments of a PrP nucleic acid such that intervening or adjacent segments are not involved in the hybridization event (e.g., a loop structure, mismatch or hairpin structure).

In certain embodiments, the antisense compounds provided herein are at least 70%, at least 75%, at least 80%, at least 85%, at least 90%, at least 95%, at least 96%, at least 97%, at least 98% or at least 99% complementary to a PrP nucleic acid. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein are fully complementary (i.e, 100% complementary) to a target nucleic acid. For example, antisense compound may be fully complementary to a PrP nucleic acid, or a target region, or a target segment or target sequence thereof. As used herein, "fully complementary" means each nucleobase of an antisense compound is capable of precise base pairing with the corresponding nucleobases of a target nucleic acid.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In certain embodiments, non-complementary nucleobase is located in the wing segment of a gapmer antisense oligonucleotide.

In certain embodiments, antisense compounds up to 20 nucleobases in length comprise no more than 4, no more than 3, no more than 2 or no more than 1 non-complementary nucleobase(s) relative to a target nucleic acid, such as a PrP nucleic acid.

In certain embodiments, antisense compounds up to 30 nucleobases in length comprise no more than 6, no more than 5, no more than 4, no more than 3, no more than 2 or no more than 1 non-complementary nucleobase(s) relative to a target nucleic acid, such as a PrP nucleic acid.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

In certain embodiments, the antisense compounds provided herein include those comprising a portion which consists of at least 8, 9, 10, 11, 12, 13, 14, 15, 16, 17, 18, 19, or contiguous nucleobases of the nucleobase sequence set forth in SEQ ID NOs: 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39. In certain embodiments, the antisense compounds are complementary to an equal-length portion of SEQ ID NOs: 1 or 2. In certain embodiments, the antisense compounds are at least 75%, 80%, 85%, 90%, 95%, or 100% (fully) complementary to SEQ ID NOs: 1 or 2.

Identity

The antisense compounds provided herein may also have a defined percent identity to a particular nucleotide sequence, SEQ ID NO, or compound represented by a specific Isis number. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have Identical base pairing relative to the sequence to which it is being compared.

In certain embodiments, the antisense compounds are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a PRP nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R$_1$)(R$_2$) for the ring oxygen at the 4'-position. Modified sugars include, but are not limited to: substituted sugars, especially 2'-substituted sugars having a 2'-F, 2'-OCH$_2$ (2'-OMe) or a 2'-O(CH$_2$)$_2$—OCH$_3$ (2'-O-methoxyethyl or 2'-MOE) substituent group; and bicyclic modified sugars (BNAs), having a 4'-(CH$_2$)$_n$—O-2' bridge, where n=1 or n=22, including α-L-Methyleneoxy (4'-CH2-O-2') BNA, β-D-Methyleneoxy (4'-CH2-O-2') BNA and Ethyleneoxy (4'-(CH2)2-O-2') BNA. Bicyclic modified sugars also include (6'S)-6' methyl BNA, Aminooxy (4'-CH2-O—N(R)-2') BNA, Oxyamino (4'-CH2-N(R)—O-2') BNA wherein, R is, independently, H, a protecting group, or C1-C12 alkyl. The substituent at the 2' position can also be selected from alyl, amino, azido, thio, O-allyl, O—C1-C10 alkyl, OCF3, O(CH2)2SCH3, O(CH2)2-O—N(Rm)(Rn), and O—CH2-C(=O)—N(Rm)(Rn), where each Rm and Rn is, independently, H or substituted or unsubstituted C1-C10 alkyl. Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a PRP nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a PrP nucleic acid comprise one or more modified nucleobases. In certain embodiments, gap-widened antisense oligonucleotides targeted to a PrP nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a PrP nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in certain embodiments, employed in the methods described herein is a pharmaceutical composition comprising an antisense compound targeted to a PrP nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

In certain embodiments, it is beneficial to deliver an antisense oligonucleotide targeted to prion to the central nervous system (CNS) of an individual suffering from prion disease or a conformational neurodgenerative disorder. Because the blood-brain barrier is generally impermeable to antisense oligonucleotides administered systemically, antisense oligonucleotides may be delivered to the tissues of the CNS. In certain embodiments, administration of antisense oligonucleotides is directly into the cerebrospinal fluid (CSF). In certain embodiments, delivery to the CSF is achieved by intrathecal administration and intracerebroventricular administration. Intracerebroventricular or intrathecal administration may be achieved through the use of surgically implanted pumps that infuse a therapeutic agent, such as an antisense oligonucleotide, into the CSF. In certain embodiments, an infusion pump may be used. In certain embodiments, the antisense oligonucleotide is continuously infused into the CSF for the entire course of treatment. In certain embodiments, antisense oligonucleotide are delivered to the CSF with an infusion pump such as Medtronic SyncroMed® II pump. The SyncroMed® II pump is surgically implanted according the procedures set forth by the manufacturer. The pump contains a reservoir for retaining one or more a drug solutions, which are pumped at a programmed dose into a catheter that is surgically implanted.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of PrP nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, Hep3B cells and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE® (Invitrogen, Carlsbad, Calif.). Antisense oligonucleotide is mixed with LIPOFECTAMINE® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 μg/μL per 100 nM antisense oligonucleotide.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 500 nM.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression Inhibition of levels or expression of a PrP nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invetrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a PrP nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of PrP nucleic acids can be assessed by measuring PrP protein levels. Protein levels of PrP can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, histone deacytelase activity), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of PrP and produce phenotypic changes, such as reduction in aggregates, increase in lifespan, improved cognitive ability, and improved motor function. Aggregates may be measured by immunoblot or histoblot. Lifespan may be measured by increased length of life of a treated animal in comparison to a non-treated animal. Cognitive ability may be measured by the Morris water maze test. Motor function may be measured using a rotarod test.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intracranial, intracerebroventricular, intraperitoneal, intravenous, and subcutaneous. Following a period of treatment with antisense oligonucleotides, RNA is isolated from a relevant tissue (e.g., liver tissue for systemic delivery and brain tissue for CNS delivery) and changes in PrP nucleic acid expression are measured.

Certain Indications

In certain embodiments, the invention provides methods of treating an individual comprising administering one or more pharmaceutical compositions of the present invention. In certain embodiments, the individual has a prion disease. In certain embodiments, the prion disease is Creutzfeldt-Jakob disease (CJD); variant Creutzfeldt-Jakob Disease (vCJD); Gerstmann-Straussler-Scheinker syndrome; fatal familial insomnia; kuru; Bovine Spongiform Encephalopathy (BSE), e.g. "mad cow disease"; Chronic Wasting Disease (CWD); scrapie; transmissible mink encephalopathy; feline spongiform encephalopathy; or ungulate spongiform encephalopathy. In certain embodiments, the individual has a conformational neurodegenerative disorder. In certain embodiments the conformational neurodegenerative disorder is Alzheimer's disease, Parkinson's disease, Huntington's disease, or Amyotrophic Lateral Sclerosis (ALS).

In certain embodiments, administration of a therapeutically effective amount of an antisense compound targeted to a PrP nucleic acid is accompanied by monitoring phenotypic changes, such as, reduction in aggregates, increase in lifespan, improved cognitive ability, and improved motor function. An individual's response to administration of the antisense compound is used by a physician to determine the amount and duration of therapeutic intervention.

In certain embodiments, administration of an antisense compound targeted to a PrP nucleic acid results in reduction of PrP expression by at least 5, 10, 15, 20, 25, 30, 35, 40, 45, 50, 55, 60, 65, 70, 75, 80, 85, 90, 95, 96, 97, 98, 99, or 100%, or a range defined by any two of these values. In certain embodiments, administration of an antisense compound targeted to a PrP nucleic acid results in phenotypic changes in an animal, such as, reduction in aggregates, increase in lifespan, improved cognitive ability, and improved motor function.

In certain embodiments, administration of an antisense compound targeted to a PrP nucleic acid in an animal results in reduction of aggregates in the animal by at least 5, 10, 15, 20, 25, 30, 35, 40, 45, 50, 55, 60, 65, 70, 75, 80, 85, 90, 95, 96, 97, 98, 99, or 100%, or a range defined by any two of these values, as compared to a non-treated animal.

In certain embodiments, administration of an antisense compound targeted to a PrP nucleic acid in an animal results in an increase in the animal's lifespan by days, weeks, months, years, or decades, as compared to a non-treated animal. In certain embodiments, the animal's lifespan is increased by at least 1, 2, 3, 4, 5, 6, or 7 days. In certain embodiments, the animal's lifespan is increased by at least 1, 2, 3, 4, or 5 weeks. In certain embodiments, the animal's lifespan is increased by at least 1, 2, 3, 4, 5, 6, 7, 8, 9, 10, 11, or 12 months. In certain embodiments, the animal's lifespan is increased by at least 1, 2, 3, 4, 5, 6, 7, 8, 9, or 10 years. In certain embodiments, the animal's lifespan is increased by at least 1, 2, 3, 4, 5, 6, 7, 8, 9, or 10 decades. In certain embodiments, administration of an antisense compound targeted to a PrP nucleic acid in an animal cures the animal.

In certain embodiments, administration of an antisense compound targeted to a PrP nucleic acid in an animal results in improved cognitive ability by at least 5, 10, 15, 20, 25, 30, 35, 40, 45, 50, 55, 60, 65, 70, 75, 80, 85, 90, 95, 96, 97, 98, 99, or 100%, or a range defined by any two of these values, as compared to a non-treated animal.

In certain embodiments, administration of an antisense compound targeted to a PrP nucleic acid in an animal results in improved motor function by at least 5, 10, 15, 20, 25, 30, 35, 40, 45, 50, 55, 60, 65, 70, 75, 80, 85, 90, 95, 96, 97, 98, 99, or 100%, or a range defined by any two of these values, as compared to a non-treated animal.

In certain embodiments a pharmaceutical composition comprising an antisense compound targeted to PrP is used for the preparation of a medicament for treating a patient suffering or susceptible to a neurodegenerative disorder.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that may be co-administered with a pharmaceutical composition of the present invention include analgesics, such as, paracetamol (acetaminophen); non-steroidal anti-inflammatory drugs (NSAIDs), such as, salicylates; narcotic drugs, such as, morphine, and synthetic drugs with narcotic properties such as tramadol.

In certain embodiments, pharmaceutical agents that may be co-administered with a pharmaceutical composition of the present invention include muscle relaxants, such as, benzodiapines and methocarbamol.

In certain embodiments, the second compound is administered prior to administration of a pharmaceutical composition of the present invention. In certain embodiments, the second compound is administered following administration of a pharmaceutical composition of the present invention. In certain embodiments, the second compound is administered at the same time as a pharmaceutical composition of the present invention. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

The in vivo studies provided herein below are carried out in well characterized animal models that are recognized by

Example 1

Antisense Inhibition of Human Prion mRNA in T-24 Cell Line

Antisense oligonucleotides targeted to a human prion protein (p27-30) mRNA were tested for their effects on prion protein (PrP) mRNA in vitro. Cultured T-24 cells at a density of 85 cells per well were treated with 100 nM antisense oligonucleotide. After a treatment period of approximately 24 hours, RNA was isolated from the cells and PrP mRNA levels were measured by quantitative real-time PCR(RT-PCR). Human primer probe set HTS 3358 was used to measure mRNA levels. PrP mRNA levels were adjusted according to total RNA content, as measured by RIBOGREEN®. Results are presented as percent inhibition of PrP mRNA, relative to untreated control cells.

All antisense oligonucleotides in Table 1 are chimeric oligonucleotides ('gapmers') 20 nucleotides in length, composed of a central 'gap' region consisting of ten 2'-deoxynucleotides, which is flanked on both sides (5' and 3' directions) by five-nucleotide 'wings'. The wings are composed of 2'-methoxyethyl (2'-MOE) nucleotides. The internucleoside (backbone) linkages are phosphorothioate (P=S) throughout the oligonucleotide. All cytidine residues are 5-methylcytidines. 'Target start site' indicates the 5'-most nucleotide to which the antisense oligonucleotide is targeted in SEQ ID NO: 1 (GENBANK Accession No. NM_000311.3). 'Target stop site' indicates the 3'-most nucleotide to which the antisense oligonucleotide is targeted in SEQ ID NO: 1.

TABLE 1

Percent inhibition of PrP expression relative to control cells

| Oligo ID | Target Seq ID NO | Target Start Site | Target Stop Site | Oligonucleotide Sequence | % Inhibition | SEQ ID NO |
|---|---|---|---|---|---|---|
| 169730 | 1 | 785 | 804 | GTCACTGCCGAAATGTATGA | 84 | 3 |
| 169731 | 1 | 817 | 836 | TGCATGTTTTCACGATAGTA | 89 | 4 |
| 169732 | 1 | 1739 | 1758 | TGTTGAACAGCTGCTGTGTA | 89 | 5 |
| 169733 | 1 | 469 | 488 | GGGTATCGGCTGCCCCCAGT | 83 | 6 |
| 169734 | 1 | 955 | 974 | GTCTCGGTGAAGTTCTCCCC | 72 | 7 |
| 169735 | 1 | 1788 | 1807 | TGAATATGTCCTCTAGCCAG | 66 | 8 |
| 169736 | 1 | 1828 | 1847 | TCCCAGAAGCCTTTCATATA | 89 | 9 |
| 169737 | 1 | 1111 | 1130 | CCCACTATCAGGAAGATGAG | 60 | 10 |
| 169738 | 1 | 1665 | 1684 | ATGCTCCAGCGGGCTGAGCC | 47 | 11 |
| 169739 | 1 | 2555 | 2574 | TTCAGTGCACATTGTAAGCC | 83 | 12 |
| 169740 | 1 | 1190 | 1209 | AAGGGCTGCAGGTGGATACC | 59 | 13 |
| 169741 | 1 | 2383 | 2402 | TAGATACTCACAAAGTGCAA | 21 | 14 |
| 169742 | 1 | 2452 | 2471 | CTGCTCTAAACAAAACTCCT | 67 | 15 |
| 169743 | 1 | 1465 | 1484 | GGTATCCAGGCAAAGGTATT | 74 | 16 |
| 169744 | 1 | 1644 | 1663 | GCATCCCAAGAGCTAAGAAT | 71 | 17 |
| 169745 | 1 | 708 | 727 | CAGCTGCTGCAGCACCAGCC | 83 | 18 |
| 169746 | 1 | 1361 | 1380 | GTTATACTTTTACTGGCCTG | 92 | 19 |
| 169747 | 1 | 2111 | 2130 | ATGCAAGCAGTTCTTTTCTT | 88 | 20 |
| 169748 | 1 | 474 | 493 | GCCCCGGGTATCGGCTGCCC | 8 | 21 |
| 169749 | 1 | 1464 | 1483 | GTATCCAGGCAAAGGTATTT | 86 | 22 |
| 169750 | 1 | 2610 | 2629 | TGCATATTTCAAAGACCTGT | 94 | 23 |
| 169751 | 1 | 1648 | 1667 | GCCTGCATCCCAAGAGCTAA | 88 | 24 |
| 169752 | 1 | 1348 | 1367 | TGGCCTGGCATTAGCAACGG | 87 | 25 |
| 169753 | 1 | 1906 | 1925 | GCCACATATAGGGTCCTTTA | 92 | 26 |
| 169754 | 1 | 2530 | 2549 | ACCACGCAAAAGGGTTTCCC | 0 | 27 |
| 169755 | 1 | 1868 | 1887 | TTGCCTCCAAGGGCACCATT | 19 | 28 |

TABLE 1-continued

Percent inhibition of PrP expression relative to control cells

| Oligo ID | Target Seq ID NO | Target Start Site | Target Stop Site | Oligonucleotide Sequence | % Inhibition | SEQ ID NO |
|---|---|---|---|---|---|---|
| 169756 | 1 | 2508 | 2527 | ATATTAAGTATTCAGTACCT | 80 | 29 |
| 169757 | 1 | 1652 | 1671 | CTGAGCCTGCATCCCAAGAG | 84 | 30 |
| 169758 | 1 | 1359 | 1378 | TATACTTTTACTGGCCTGGC | 0 | 31 |
| 169759 | 1 | 1658 | 1677 | AGCGGGCTGAGCCTGCATCC | 3 | 32 |
| 169760 | 1 | 801 | 820 | AGTAACGGTCCTCATAGTCA | 81 | 33 |
| 169761 | 1 | 690 | 709 | CCATGTGCTTCATGTTGGTT | 56 | 34 |
| 169762 | 1 | 818 | 837 | GTGCATGTTTTCACGATAGT | 62 | 35 |
| 169763 | 1 | 2152 | 2171 | CTAATTCTGGTTTTTGACAA | 76 | 36 |
| 169764 | 1 | 1897 | 1916 | AGGGTCCTTTAAACATCTAA | 92 | 37 |
| 169765 | 1 | 1047 | 1066 | TGCTCGATCCTCTCTGGTAA | 56 | 38 |
| 169766 | 1 | 1094 | 1113 | GAGGAAAGAGATCAGGAGGA | 60 | 39 |

Example 2

Dose-Dependent Antisense Inhibition of Mouse PrP mRNA in the Mouse b-END Cell Line Chimeric antisense oligonucleotides having 5-10-5 wings and deoxy gap, and a phosphorothioate backbone were designed to target murine PrP (GENEBANK Accession No. NM_011170.1), incorporated herein as SEQ ID NO: 2. The oligonucleotides ('gapmers') are 20 nucleotides in length, composed of a central 'gap' region consisting of ten 2'-deoxynucleotides, which is flanked on both sides (5' and 3' directions) by five-nucleotide 'wings'. The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The antisense oligonucleotides were evaluated for their ability to reduce murine PrP (p27-30) (moPrP) mRNA in mouse b.END cells.

Antisense oligonucleotides ISIS 398742 (TATATTCTTATTGGCCCGGT, target site 1142), incorporated herein as SEQ ID NO: 40; ISIS 398747 (GCCTATGCTAAGTTACATGT, target site 1262), incorporated herein as SEQ ID NO: 41; and ISIS 398771 (CCAAGGGTCACACGGTAAGC, target site 1961), incorporated herein as SEQ ID NO: 42, targeted to moPrP (NM_011170.1; SEQ ID NO: 2), were tested at various doses in b-END cell line. Cells were plated at densities of 4,000 cells per well and treated with 6.25 nM, 12.5 nM, 25 nM, 50 nM, 100 nM, and 200 nM concentrations of antisense oligonucleotide, as indicated in Table 2. After a treatment period of approximately 24 hours, RNA was isolated from the cells and moPrP mRNA levels were measured by quantitative real-time RT-PCR, as described herein. Murine primer probe set RTS 2792 was used to measure mRNA levels. moPrP mRNA levels were adjusted according to total RNA content, as measured by RIBOGREEN®. Results are expressed as percent inhibition of PrP, relative to control cells incubated with PBS. As illustrated in Table 2, PrP mRNA levels were reduced in a dose-dependent manner.

TABLE 2

Percent inhibition of mouse PrP expression relative to control cells

| ISIS No. | 6.25 nM | 12.5 nM | 25 nM | 50 nM | 100 nM | 200 nM |
|---|---|---|---|---|---|---|
| 398742 | 41 | 57 | 79 | 86 | 93 | 94 |
| 398747 | 34 | 53 | 82 | 95 | 98 | 97 |
| 398771 | 28 | 48 | 73 | 91 | 95 | 97 |

As shown in Table 2, percent inhibition of moPrP expression in mouse b-END cells is dose dependent, thus indicating that significant inhibition of PrP expression can be achieved by the administration of ISIS antisense oligonucleotides targeting moPrP.

Example 3

Antisense Inhibition of Mouse PrP In Vivo

Treatment

Antisense oligonucleotides, ISIS 398742, ISIS 398747, and ISIS 398771 were evaluated for their ability to reduce the mouse prion protein, moPrP in vivo.

RNA Analysis

Antisense oligonucleotides, ISIS 398742, 398747 and 398771 were examined in a group of 5 FVB mice and compared to a control group treated with PBS. Oligonucleotide or PBS was administered intraperitoneally at a dose of 50 mg/kg and 100 mg/kg twice a week for 3 weeks. After the treatment period, mouse livers were harvested for RNA analysis. Treatment with ISIS 398742, 398747, and 398771 resulted in statistically significant dose-dependent reduction of moPrP mRNA in comparison to the control PBS sample.

As shown in Table 3, treatment with ISIS 398742, ISIS 398747, and ISIS 398771 resulted in a dose-dependent reduction of moPrP mRNA, as compared to the PBS control. Results were normalized with cyclophilin and are shown as percentage reduction over the control.

TABLE 3

Dose-dependent inhibition of moPrP mRNA expression

| ISIS | Dose (mg/kg/wk) | % inhibition |
|---|---|---|
| 398742 | 50 | 73 |
| 398742 | 100 | 81 |
| 398747 | 50 | 0 |
| 398747 | 100 | 35 |
| 398771 | 50 | 34 |
| 398771 | 100 | 65 |

Protein Analysis

Antisense oligonucleotides ISIS 398742, ISIS 398747, and ISIS 398771 were examined in groups of 5 mice each and compared to a control group treated with PBS. Oligonucleotide or PBS was administered at a dose of 50 mg/kg or 100 mg/kg twice a week for 3 weeks. After the treatment period, mouse livers were harvested for protein analysis. Treatment with ISIS 398742, ISIS 398747, and ISIS 398771 resulted in statistically significant reduction of moPrP protein in comparison to the PBS control (Table 4). moPrP protein was measured in the liver of mice treated with ISIS oligonucleotides with the enzyme-linked immunosorbant assay (ELISA). The anti-PrP antibody, D18, was used for detection. Results are shown as percentage reduction over the control.

TABLE 4

Dose-dependent antisense inhibition of moPrP protein

| ISIS No. | mg/kg/wk | % inhibition |
|---|---|---|
| 398742 | 50 | 65 |
| 398742 | 100 | 72 |
| 398747 | 50 | 51 |
| 398747 | 100 | 49 |
| 398771 | 50 | 53 |
| 398771 | 100 | 36 |

Example 4

Antisense Inhibition of moPrP in ScN2a Cell Line

ScN2a cells, expressing the infectious isoform of the prion protein, were divided into 3 sets and incubated continuously for 48 hours with 500 nM each of ISIS 398742, 398747, or 398771, without lipofectamine reagent. After the treatment period, the various treated and PBS control cell sets were harvested and treated with proteinase K (PK). Western analysis of the lysates was performed with D18 antibody. Table 5 shows the percent inhibition of protein expression as measured by intensity of the PrPSc band in the oligonucleotide-treated cells compared to the control cells.

TABLE 5

Percent inhibition of PrPSc protein expression

| ISIS | % inhibition |
|---|---|
| 398742 | 82 |
| 398747 | 64 |
| 398771 | 59 |

Example 5

Antisense Inhibition of Mouse PrP by ICV Infusion In Vivo

RNA Analysis

ISIS 398742 and 398771 were administered intracerebroventricularly (ICV) to groups of 4 mice each via a 2002 Alzet pump at a continuous dose of 75 µg per day for 2 weeks. A control set of mice was injected with PBS ICV for the same duration. After the treatment period brain sections were harvested, RNA was isolated, and RT-PCR analysis for moPrP mRNA was performed. Table 6 shows the inhibition of moPrP mRNA after treatment with ISIS oligonucleotides. Results are expressed as percent inhibition over the PBS control.

TABLE 6

Antisense inhibition of moPrP mRNA via ICV infusion of antisense oligonucleotides

| ISIS | % inhibition |
|---|---|
| 398742 | 27 |
| 398771 | 43 |

Protein Analysis

ISIS 398742 and 398771 were administered ICV to groups of 4 mice each via a 2002 Alzet pump at a continuous dose of 75 µg per day for 2 weeks. A control set of mice was injected with PBS ICV for the same duration. Brain tissue was harvested and PrP protein expression was measured by ELISA. Table 7 shows the percent reduction of PrP protein after treatment. Results are expressed as percent inhibition over the PBS control.

TABLE 7

Antisense inhibition of moPrP protein via ICV infusion of antisense oligonucleotides

| ISIS | % inhibition |
|---|---|
| 398742 | 27 |
| 398771 | 45 |

Example 6

Dose-Dependent Antisense Inhibition of Mouse PrP by ICV Infusion In Vivo

To assess the tolerance of a continuous dosage of antisense oligonucleotides via ICV injection, ISIS 398771 was administered ICV to groups of 4 mice each via a 2002 Alzet pump at a continuous dose of 25, 50, 75, and 100 µg per day for 2 weeks. A control group of mice were injected with PBS for the same duration of time. At the end of the treatment period, RNA was isolated from the brain of each animal and RT-PCR analysis performed. Table 8 shows the dose-dependent reduction of moPrP mRNA after administration of the antisense oligonucleotides compared to the control.

TABLE 8

Dose-dependent inhibition of moPrP mRNA via
ICV infusion of antisense oligonucleotides

|  | ug/day | % inhibition |
|---|---|---|
| 398771 | 25 | 53 |
| 398771 | 50 | 59 |
| 398771 | 75 | 66 |
| 398771 | 100 | 71 |

ISIS 398771 was well tolerated and was non-toxic with a dose of 100 µg/day, producing 71% knockdown of brain PrP mRNA expression levels compared to the PBS control. ISIS 398771 was therefore used in further studies for antisense inhibition of moPrP.

Example 7

Prophylactic Study of ISIS 398771 by ICV Infusion
In Vivo Before RML Scrapie (PrPSc) Inoculation A group of FVB mice weighing 20 g can be inoculated with PrPSc (RML scrapie) in the thalamus and may be allowed to recover for 2 days. The resulting RML scrapie model can be used for subsequent study.

RML scrapie mice can then be cannulated in the right side of the lateral ventricle with an Alzet. ISIS 398771 can be administered to the RML scrapie mice via Alzet pump. Control RML scrapie mice can be treated with PBS. Mice can be sacrificed at different time points to study the spread of PrPSc throughout the brain. Spread of PrPSc can be evaluated using the histoblot method cited in Hecker, R, et al., *Genes Dev*, 6, 1213-28, 1992 and Tatzelt, J, et al., *J Neuropathol Exp Neurol*, 58, 1244-9, 1999. Spread of PrPSc can also be evaluated by size and location of aggregates. Aggregates may be measured by Western blot or histoblot.

ISIS 398771 treated mice can be evaluated to assess delay or prevention of the spread of scrapie infection or aggregate formation in the brain during the study period.

Example 8

End Point Survival Studies in the RML Scrapie Model

The RML scrapie model can be used to determine the survival rate of mice with or without treatment with ISIS 398771.

RML scrapie mice can then be cannulated in the right side of the lateral ventricle with an Alzet. ISIS 398771 can be administered to the RML scrapie mice via Alzet pump. Control RML scrapie mice can be treated with PBS. Both groups of mice may are allowed to age and the survival rates of mice is be monitored.

The average survival of RML scrapie mice is around 120 days after infection. ISIS 398771 treated mice can be monitored to determined if they can live for days, weeks, or months longer than control mice.

What is claimed is:

1. A modified antisense oligonucleotide consisting of 12 to 30 linked nucleosides, wherein the modified antisense oligonucleotide is a gapmer and is fully complementary to an equal number of consecutive nucleobases selected from 469 to 2629 of the human PrP nucleic acid of SEQ ID NO:1.

2. The modified antisense oligonucleotide of claim 1, wherein the modified oligonucleotide is a single-stranded oligonucleotide.

3. The modified antisense oligonucleotide of claim 2, wherein at least one internucleoside linkage is a modified internucleoside linkage.

4. The modified antisense oligonucleotide of claim 3, wherein each internucleoside linkage is a phosphorothioate internucleoside linkage.

5. The modified antisense oligonucleotide of claim 4, wherein at least one nucleoside comprises a modified sugar.

6. The modified antisense oligonucleotide of claim 5, wherein at least one modified sugar is a bicyclic sugar.

7. The modified antisense oligonucleotide of claim 5, wherein at least one modified sugar is a 2′-O-methoxyethyl.

8. The modified antisense oligonucleotide of claim 2, wherein at least one nucleoside comprises a modified nucleobase.

9. The modified antisense oligonucleotide of claim 8, wherein the modified nucleobase is a 5-methylcytosine.

10. A method of inhibiting expression of PrP an animal, comprising administering to the animal the modified antisense oligonucleotide of claim 1.

11. A modified antisense oligonucleotide consisting of 12 to 30 linked nucleosides, wherein the modified antisense oligonucleotide is fully complementary to an equal number of consecutive nucleobases selected from 469 to 2629 of the human PrP nucleic acid of SEQ ID NO: 1.

12. The modified antisense oligonucleotide of claim 11, wherein the modified oligonucleotide is a single-stranded oligonucleotide.

13. The modified antisense oligonucleotide of claim 12, wherein at least one internucleoside linkage is a modified internucleoside linkage.

14. The modified antisense oligonucleotide of claim 13, wherein each internucleoside linkage is a phosphorothioate internucleoside linkage.

15. The modified antisense oligonucleotide of claim 14, wherein at least one nucleoside comprises a modified sugar.

16. The modified antisense oligonucleotide of claim 15, wherein at least one modified sugar is a bicyclic sugar.

17. The modified antisense oligonucleotide of claim 15, wherein at least one modified sugar is a 2′-O-methoxyethyl.

18. The modified antisense oligonucleotide of claim 12, wherein at least one nucleoside comprises a modified nucleobase.

19. The modified antisense oligonucleotide of claim 18, wherein the modified nucleobase is a 5-methylcytosine.

20. The modified antisense oligonucleotide of claim 6, wherein the bicyclic sugar is a (6′S)-6′methyl BNA.

21. The modified antisense oligonucleotide of claim 16, wherein the bicyclic sugar is a (6′S)-6′methyl BNA.

22. A method of inhibiting expression of PrP in an animal, comprising administering to the animal the modified antisense oligonucleotide of claim 11.

23. The modified antisense oligonucleotide of claim 1, wherein said modified antisense oligonucleotide consists of 15 to 30, 18 to 24, or 19 to 22 linked nucleosides.

24. The modified antisense oligonucleotide of claim 1, wherein said modified antisense oligonucleotide consists of 20 linked nucleosides.

25. The modified antisense oligonucleotide of claim 11, wherein said modified antisense oligonucleotide consists of 15 to 30, 18 to 24, or 19 to 22 linked nucleosides.

26. The modified antisense oligonucleotide of claim 11, wherein said modified antisense oligonucleotide consists of 20 linked nucleosides.

27. The modified antisense oligonucleotide of claim 1, wherein the gap segment of the oligonucleotide consists of 2-deoxynucleotides and wherein each wing segment of the oligonucleotide consists of 2-O-methoxyethyl-modified nucleotides.

28. The method of claim 10, wherein the gap segment of the oligonucleotide consists of 2-deoxynucleotides and wherein each wing segment of the oligonucleotide consists of 2′-O-methoxyethyl-modified nucleotides.

29. The modified antisense oligonucleotide of claim 23, wherein the gap segment of the oligonucleotide consists of 2′-deoxynucleotides and wherein each wing segment of the oligonucleotide consists of 2′-O-methoxyethyl-modified nucleotides.

30. The modified antisense oligonucleotide of claim 24, wherein the gap segment of the oligonucleotide consists of 2′-deoxynucleotides and wherein each wing segment of the oligonucleotide consists of 2′-O-methoxyethyl-modified nucleotides.

* * * * *

SEQUENCE LISTING

<160> NUMBER OF SEQ ID NOS: 42

<210> SEQ ID NO 1
<211> LENGTH: 2755
<212> TYPE: DNA
<213> ORGANISM: Homo sapiens

<400> SEQUENCE: 1

```
attaaagatg atttttacag tcaatgagcc acgtcaggga gcgatggcac ccgcaggcgg      60
tatcaactga tgcaagtgtt caagcgaatc tcaactcgtt ttttccggtg actcattccc     120
ggccctgctt ggcagcgctg caccctttaa cttaaacctc ggccggccgc ccgcggggg     180 cacagagtgt gcgccgggcc gcgcggcaat tggtccccgc gccgacctcc gcccgcgagc     240
gccgccgctt cccttccccg ccccgcgtcc ctcccccctcg gccccgcgcg tcgcctgtcc     300
tccgagccag tcgctgacag ccgcggcgcc gcgagcttct cctctcctca cgaccgaggc     360
agagcagtca ttatggcgaa ccttggctgc tggatgctgg ttctctttgt ggccacatgg     420
agtgacctgg gcctctgcaa gaagcgcccg aagcctggag gatggaacac tggggcagc     480 cgataccccgg ggcagggcag ccctggaggc aaccgctacc cacctcaggg cggtggtggc     540
tgggggcagc ctcatggtgg tggctggggg cagcctcatg gtggtggctg ggggcagccc     600
catggtggtg gctggggaca gcctcatggt ggtggctggg gtcaaggagg tggcacccac     660
agtcagtgga acaagccgag taagccaaaa accaacatga agcacatggc tggtgctgca     720
gcagctgggg cagtggtggg gggccttggc ggctacatgc tgggaagtgc catgagcagg     780
cccatcatac atttcggcag tgactatgag gaccgttact atcgtgaaaa catgcaccgt     840
taccccaacc aagtgtacta caggcccatg gatgagtaca gcaaccagaa caactttgtg     900
```

```
cacgactgcg tcaatatcac aatcaagcag cacacggtca ccacaaccac caaggggag      960 aacttcaccg agaccgacgt taagatgatg gagcgcgtgg ttgagcagat gtgtatcacc     1020
cagtacgaga gggaatctca ggcctattac cagagaggat cgagcatggt cctcttctcc    1080
tctccacctg tgatcctcct gatctctttc ctcatcttcc tgatagtggg atgaggaagg    1140
tcttcctgtt ttcaccatct ttctaatctt tttccagctt gagggaggcg gtatccacct    1200
gcagcccttt tagtggtggt gtctcactct ttcttctctc tttgtcccgg ataggctaat    1260
caataccctt ggcactgatg ggcactggaa aacatagagt agacctgaga tgctggtcaa    1320
gccccctttg attgagttca tcatgagccg ttgctaatgc caggccagta aaagtataac    1380
agcaaataac cattggttaa tctggactta tttttggact tagtgcaaca ggttgaggct    1440
aaaacaaatc tcagaacagt ctgaaatacc tttgcctgga tacctctggc tccttcagca    1500
gctagagctc agtatactaa tgccctatct tagtagagat ttcatagcta tttagagata    1560
ttttccattt taagaaaacc cgacaacatt tctgccaggt ttgttaggag gccacatgat    1620
acttattcaa aaaaatccta gagattctta gctcttggga tgcaggctca gcccgctgga    1680
gcatgagctc tgtgtgtacc gagaactggg gtgatgtttt acttttcaca gtatgggcta    1740
cacagcagct gttcaacaag agtaaatatt gtcacaacac tgaacctctg gctagaggac    1800
atattcacag tgaacataac tgtaacatat atgaaaggct tctgggactt gaaatcaaat    1860
gtttgggaat ggtgcccttg gaggcaacct cccatttag atgtttaaag gaccctatat     1920
gtggcattcc tttcttttaaa ctataggtaa ttaaggcagc tgaaaagtaa attgccttct   1980
agacactgaa ggcaaatctc ctttgtccat ttacctggaa accagaatga ttttgacata    2040
caggagagct gcagttgtga aagcaccatc atcatagagg atgatgtaat taaaaaatgg    2100
tcagtgtgca aagaaaagaa ctgcttgcat ttctttattt ctgtctcata attgtcaaaa    2160
accagaatta ggtcaagttc atagtttctg taattggctt ttgaatcaaa gaataggag     2220 acaatctaaa aaatatctta ggttggagat gacagaaata tgattgattt gaagtggaaa    2280
aagaaattct gttaatgtta attaaagtaa aattattccc tgaattgttt gatattgtca    2340
cctagcagat atgtattact tttctgcaat gttattattg gcttgcactt tgtgagtatt    2400
ctatgtaaaa atatatatgt atataaaata tatattgcat aggacagact taggagtttt   2460
gtttagagca gttaacatct gaagtgtcta atgcattaac ttttgtaagg tactgaatac    2520
ttaatatgtg ggaaacccctt ttgcgtggtc cttaggctta caatgtgcac tgaatcgttt   2580
catgtaagaa tccaaagtgg acaccattaa caggtctttg aaatatgcat gtactttata   2640
ttttctatat ttgtaacttt gcatgttctt gttttgttat ataaaaaaat tgtaaatgtt    2700
taatatctga ctgaaattaa acgagcgaag atgagcacca aaaaaaaaaa aaaaa         2755
```

<210> SEQ ID NO 2
<211> LENGTH: 2153
<212> TYPE: DNA
<213> ORGANISM: Mus musculus

<400> SEQUENCE: 2

```
gtcggatcag cagaccgatt ctgggcgctg cgtcgcatcg gtggcaggac tcctgagtat      60
atttcagaac tgaaccattt caaccgagct gaagcattct gccttcctag tggtaccagt    120
ccaatttagg agagccaagc agactatcag tcatcatggc gaaccttggc tactggctgc    180 tggcccctctt tgtgactatg tggactgatg tcggcctctg caaaaagcgg ccaaagcctg    240
gagggtggaa caccggtgga agccggtatc ccgggcaggg aagccctgga ggcaaccgtt    300
```

| | |
|---|---|
| acccacctca gggtggcacc tgggggcagc cccacggtgg tggctgggga caaccccatg | 360 |
| ggggcagctg gggacaacct catggtggta gttggggtca gccccatggc ggtggatggg | 420 |
| gccaaggagg gggtacccat aatcagtgga acaagcccag caaaccaaaa accaacctca | 480 |
| agcatgtggc aggggctgcg gcagctgggg cagtagtggg gggccttggt ggctacatgc | 540 |
| tggggagcgc catgagcagg cccatgatcc attttggcaa cgactgggag gaccgctact | 600 |
| accgtgaaaa catgtaccgc taccctaacc aagtgtacta caggccagtg gatcagtaca | 660 |
| gcaaccagaa caacttcgtg cacgactgcg tcaatatcac catcaagcag cacacggtca | 720 |
| ccaccaccac caaggggag aacttcaccg agaccgatgt gaagatgatg gagcgcgtgg | 780 |
| tggagcagat gtgcgtcacc cagtaccaga aggagtccca ggcctattac gacgggagaa | 840 |
| gatccagcag caccgtgctt ttctcctccc ctcctgtcat cctcctcatc tccttcctca | 900 |
| tcttcctgat cgtgggatga gggaggcctt cctgcttgtt ccttcgcatt ctcgtggtct | 960 |
| aggctggggg agggttatc cacctgtagc tctttcaatt gaggtggttc tcattcttgc | 1020 |
| ttctctgtgt cccccatagg ctaatacccc tggcactgat gggccctggg aaatgtacag | 1080 |
| tagaccagtt gctctttgct tcaggtccct ttgatggagt ctgtcatcag ccagtgctaa | 1140 |
| caccgggcca ataagaatat aacaccaaat aactgctggc tagttggggc tttgttttgg | 1200 |
| tctagtgaat aaatactggt gtatcccctg acttgtaccc agagtacaag gtgacagtga | 1260 |
| cacatgtaac ttagcatagg caaagggttc tacaaccaaa gaagccactg tttggggatg | 1320 |
| gcgccctgga aaacagcctc ccacctggga tagctagagc atccacacgt ggaattcttt | 1380 |
| ctttactaac aaacgatagc tgattgaagg caacaggaaa aaaaaaatca aattgtccta | 1440 |
| ctgacgttga aagcaaacct tgttcattc ccagggcact agaatgatct ttagccttgc | 1500 |
| ttggattgaa ctaggagatc ttgactctga ggagagccag ccctgtaaaa agcttggtcc | 1560 |
| tcctgtgacg ggagggatgg ttaaggtaca aaggctagaa acttgagttt cttcatttct | 1620 |
| gtctcacaat tatcaaaagc tagaattagc ttctgcccta tgtttctgta cttctatttg | 1680 |
| aactggataa cagagagaca atctaaacat tctcttaggc tgcagataag agaagtaggc | 1740 |
| tccattccaa agtgggaaag aaattctgct agcattgttt aaatcaggca aaatttgttc | 1800 |
| ctgaagttgc ttttaccccc agcagacata aactgcgata gcttcagctt gcactgtgga | 1860 |
| ttttctgtat agaatatata aaacataact tcaagcttat gtcttctttt taaaacatct | 1920 |
| gaagtatggg acgccctggc cgttccatcc agtactaaat gcttaccgtg tgacccttgg | 1980 |
| gctttcagcg tgcactcagt tccgtaggat tccaaagcag acccctagct ggtctttgaa | 2040 |
| tctgcatgta cttcacgttt tctatatttg taactttgca tgtattttgt tttgtcatat | 2100 |
| aaaaagttta taaatgtttg ctatcagact gacattaaat agaagctatg atg | 2153 |

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
gtcactgccg aaatgtatga                                          20

<210> SEQ ID NO 4
<211> LENGTH: 20
<212> TYPE: DNA
<213> ORGANISM: Artificial Sequence
<220> FEATURE:

<223> OTHER INFORMATION: Synthetic Oligonucleotide

<400> SEQUENCE: 4
tgcatgtttt cacgatagta                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
tgttgaacag ctgctgtgta                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
gggtatcggc tgcccccagt                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
gtctcggtga agttctcccc                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
tgaatatgtc ctctagccag                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
tcccagaagc ctttcatata                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
cccactatca ggaagatgag                                              20

<210> SEQ ID NO 11

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
atgctccagc gggctgagcc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
ttcagtgcac attgtaagcc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
aagggctgca ggtggatacc                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
tagatactca caaagtgcaa                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
ctgctctaaa caaaactcct                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
ggtatccagg caaaggtatt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
```

-continued gcatcccaag agctaagaat                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 18
cagctgctgc agcaccagcc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
gttatacttt tactggcctg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
atgcaagcag ttcttttctt                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
gccccgggta tcggctgccc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
gtatccaggc aaaggtattt                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
tgcatatttc aaagacctgt                                              20

<210> SEQ ID NO 24
<211> LENGTH: 20
<212> TYPE: DNA
<213> ORGANISM: Artificial Sequence
<220> FEATURE:

-continued

<223> OTHER INFORMATION: Synthetic Oligonucleotide

<400> SEQUENCE: 24
gcctgcatcc caagagctaa                                                20

<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
tggcctggca ttagcaacgg                                                20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
gccacatata gggtccttta                                                20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
accacgcaaa agggtttccc                                                20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
ttgcctccaa gggcaccatt                                                20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
atattaagta ttcagtacct                                                20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
ctgagcctgc atcccaagag                                                20

<210> SEQ ID NO 31

-continued

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 31 tatacttttia ctggcctggc                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
agcgggctga gcctgcatcc                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
agtaacggtc ctcatagtca                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
ccatgtgctt catgttggtt                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
gtgcatgttt tcacgatagt                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
ctaattctgg tttttgacaa                                               20

<210> SEQ ID NO 37
<211> LENGTH: 20
<212> TYPE: DNA
```

```
<213> ORGANISM: Artificial Sequence
<220> FEATURE:
<223> OTHER INFORMATION: Synthetic Oligonucleotide

<400> SEQUENCE: 37
agggtccttt aaacatctaa                                           20

<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
tgctcgatcc tctctggtaa                                           20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
gaggaaagag atcaggagga                                           20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
tatattctta ttggcccggt                                           20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
gcctatgcta agttacatgt                                           20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
ccaagggtca cacggtaagc                                           20
```